(12) United States Patent
Lynn

(10) Patent No.: US 11,820,684 B1
(45) Date of Patent: Nov. 21, 2023

(54) SYSTEM FOR GENERATING AQUEOUS OZONE SOLUTION WITH INTERNAL CRADLE FOR MOUNTING AND ISOLATING ELECTRONIC COMPONENTS

(71) Applicant: Daniel W. Lynn, Omaha, NE (US)

(72) Inventor: Daniel W. Lynn, Omaha, NE (US)

(*) Notice: Subject to any disclaimer, the term of this patent is extended or adjusted under 35 U.S.C. 154(b) by 0 days.

(21) Appl. No.: 18/230,757

(22) Filed: Aug. 7, 2023

Related U.S. Application Data

(63) Continuation-in-part of application No. 18/326,188, filed on May 31, 2023, which is a continuation-in-part of application No. 17/727,278, filed on Apr. 22, 2022, now Pat. No. 11,713,265, which is a continuation of application No. 17/505,000, filed on Oct. 19, 2021, now Pat. No. 11,312,644, which is a continuation-in-part of application No. 17/378,977, filed on Jul. 19, 2021, now Pat. No. 11,198,627, which is a continuation-in-part of application No. 17/325,966, filed on May 20, 2021, now Pat. No. 11,098,910, which is a continuation-in-part of application No. 17/200,799, filed on Mar. 13, 2021, now Pat. No. 11,045,571.

(51) Int. Cl.
*C02F 1/78* (2023.01)
*B01F 23/23* (2022.01)
*B01F 23/232* (2022.01)
*B01F 23/237* (2022.01)

(52) U.S. Cl.
CPC ............... *C02F 1/78* (2013.01); *B01F 23/23* (2022.01); *B01F 23/232* (2022.01); *B01F 23/237613* (2022.01); *C02F 2201/782* (2013.01); *C02F 2209/04* (2013.01); *C02F 2303/04* (2013.01)

(58) Field of Classification Search
CPC .......... C02F 1/78; B01F 23/23; B01F 23/232
See application file for complete search history.

(56) References Cited

U.S. PATENT DOCUMENTS 5,853,014 A    12/1998  Rosenauer
6,153,105 A    11/2000  Tadlock et al.
(Continued)

FOREIGN PATENT DOCUMENTS

| ES | 1174333 U | 1/2017 | |
|---|---|---|---|
| WO | WO-0023383 A1 * | 4/2000 | .......... B01F 15/0437 |
| WO | WO-2013025660 A1 * | 2/2013 | ............ A61L 2/202 |

*Primary Examiner* — Robert A Hopkins
(74) *Attorney, Agent, or Firm* — Nasr Patent Law LLC; Faisal K. Abou-Nasr

(57) ABSTRACT

A system for generating aqueous ozone solution (AOS) is disclosed. The system includes a system enclosure and a cradle mounted within the system enclosure. The cradle has a wall that defines separate compartments within the system enclosure, including a first compartment for electronic components and a second compartment for a fluid path extending from a water inlet to an AOS outlet. The first compartment contains an ozone generator and a relay mounted to the cradle. The fluid path within the second compartment includes a fluid mixer that is coupled to the ozone generator via one or more tubes extending across (e.g., over or through) the cradle wall that separates the first and second compartments. The fluid mixer is configured to inject ozone generated by the ozone generator into water received from a water source via the water inlet to produce AOS that is output via the AOS outlet.

20 Claims, 7 Drawing Sheets

(56) References Cited

U.S. PATENT DOCUMENTS

| | | |
|---|---|---|
| 6,334,328 B1 | 1/2002 | Brill |
| 6,685,825 B1 | 2/2004 | Chang |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn et al. |
| 2002/0127158 A1 | 9/2002 | Holsclaw et al. |
| 2003/0209502 A1 | 11/2003 | Lacasse et al. |
| 2004/0004042 A1 | 1/2004 | Hadley et al. |
| 2004/0074252 A1 | 4/2004 | Shelton |
| 2004/0168989 A1 | 9/2004 | Tempest et al. |
| 2009/0142225 A1 | 6/2009 | Tornqvist |
| 2009/0185959 A1 | 7/2009 | Weber et al. |
| 2010/0219137 A1 | 9/2010 | Lacasse |
| 2013/0193081 A1 | 8/2013 | Vasiliu et al. |
| 2013/0341285 A1 | 12/2013 | Marion |
| 2014/0027388 A1 | 1/2014 | Constant |
| 2014/0263097 A1 | 9/2014 | Lynn et al. |
| 2016/0251243 A1 | 9/2016 | Lynn |

\* cited by examiner

SYSTEM FOR GENERATING AQUEOUS OZONE SOLUTION WITH INTERNAL CRADLE FOR MOUNTING AND ISOLATING ELECTRONIC COMPONENTS

CROSS-REFERENCE TO RELATED APPLICATIONS

The present application is a Continuation-in-Part of U.S. application Ser. No. 18/326,188 filed May 31, 2023 and titled "TRANSPORTABLE SYSTEM WITH VARIABLY CONTROLLED OZONE GENERATOR AND ONE OR MORE AUXILIARY COMPARTMENTS CONTAINING MIXING ASSEMBLIES FOR GENERATING AQUEOUS OZONE SOLUTION," which is a Continuation-in-Part of U.S. application Ser. No. 17/727,278 filed Apr. 22, 2022 and titled "TRANSPORTABLE OZONE SUPPLY UNIT WITH ONE OR MORE AUXILIARY COMPARTMENTS CONTAINING MIXING ASSEMBLIES FOR GENERATING AQUEOUS OZONE SOLUTION," which is a Continuation of U.S. application Ser. No. 17/505,000 filed Oct. 19, 2021 and titled "TRANSPORTABLE OZONE SUPPLY UNIT WITH ONE OR MORE AUXILIARY COMPARTMENTS CONTAINING MIXING ASSEMBLIES FOR GENERATING AQUEOUS OZONE SOLUTION," which is a Continuation-in-Part of U.S. application Ser. No. 17/378,977 filed Jul. 19, 2021 and titled "OZONE SUPPLY UNIT WITH AUXILIARY COMPARTMENT CONTAINING CONTROLLED SUCTION MIXING ASSEMBLY FOR GENERATING AQUEOUS OZONE SOLUTION," which is a Continuation-in-Part of U.S. application Ser. No. 17/325,966 filed May 20, 2021 and titled "HVAC DECONTAMINATION SYSTEM WITH REGULATED OZONE OUTPUT BASED ON MONITORED OZONE LEVEL IN AMBIENT AIR," which is a Continuation-in-Part of U.S. application Ser. No. 17/200,799 filed Mar. 13, 2021 and titled "REDUCED NOISE AIR DECONTAMINATOR," all of which are incorporated herein by reference.

TECHNICAL FIELD

The present disclosure relates to systems for generating aqueous ozone solutions.

BACKGROUND

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

There are a number of systems that generate ORP in water by injecting ozone into the water to create an ozone and water solution (often referred to as an "aqueous ozone solution"). However, high pressure water applications present challenges, often requiring the use of an intermediate tank that must be filled prior to use (much like a water heater).

Some systems generate aqueous ozone on-demand, without the use of an intermediate tank. Instead ozone is injected into water as it flows through the system. On-demand system configurations are advantageous because they tend to have a smaller footprint, but the chances of system failure increase as these systems are made smaller because electronic components and fluid paths must be placed closer and closer together. Consequently, there is a higher chance of damage to electronic components from water that may leak out of the fluid paths at high pressure.

There is a need for small footprint system configurations that allow for on-demand generation of aqueous ozone with a reduced risk of water damage to electronic components.

SUMMARY

Aspects of this disclosure are directed to a system for generating aqueous ozone solution (AOS) with structural isolation between electronic components and fluid path(s) of the system. In embodiments, the system includes a system enclosure and a cradle mounted within the system enclosure. The cradle has a wall that defines separate compartments within the system enclosure, including a first compartment for electronic components and a second compartment for a fluid path extending from a water inlet to an AOS outlet. The first compartment contains an ozone generator and a relay mounted to the cradle; the relay being configured to selectively activate the ozone generator. The fluid path within the second compartment includes a fluid mixer that is coupled to the ozone generator via one or more tubes extending across (e.g., over or through) the cradle wall that separates the first and second compartments. The fluid mixer is configured to inject ozone generated by the ozone generator into water received via the water inlet to produce AOS that is output via the AOS outlet.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The Detailed Description is provided with reference to the accompanying Drawings. The use of the same reference numbers in different instances may indicate similar or identical items. The Drawings are not necessarily to scale, and embodiments provided in the Drawings may be modified or combined to arrive at different embodiments without departing from the scope of this disclosure. Furthermore, the steps/operations of any disclosed processes may be performed in an arbitrary order, unless otherwise specified herein. In the Drawings.

DETAILED DESCRIPTION

Figure 1:
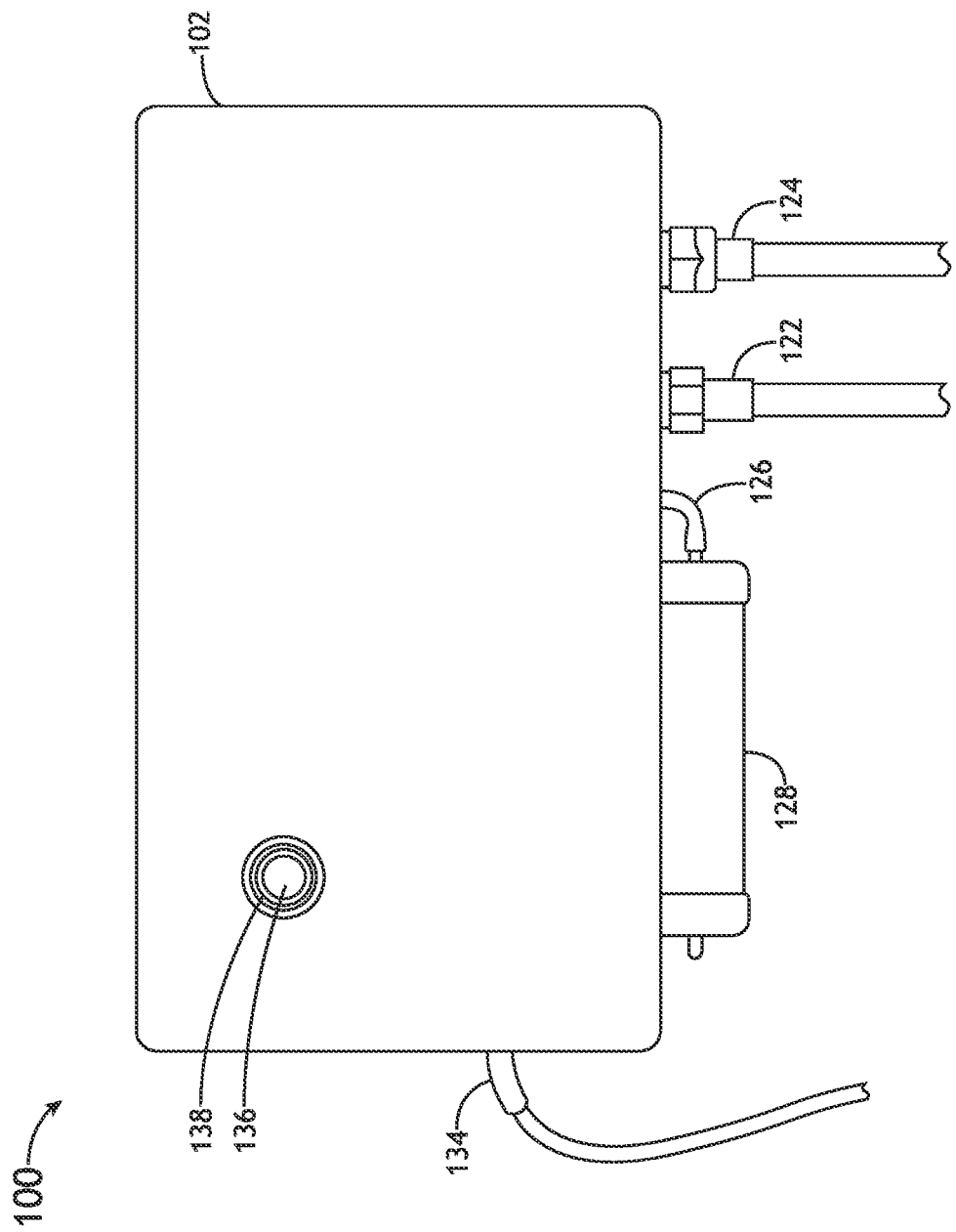
FIG. 1 is a front view of a system for generating aqueous ozone solution (AOS), in accordance with one or more embodiments of this disclosure.

Reference will now be made in detail to the subject matter disclosed, which is illustrated in the accompanying drawings.

Embodiments of this disclosure are directed to a system that generates an aqueous ozone solution (AOS) for cleaning purposes, with structural isolation between electronic components and fluid path(s) of the system. The system can be used for cleansing and/or degreasing hard surfaces such as plastic, glass, ceramic, porcelain, stainless steel, or the like. In some embodiments, the system is designed for use in a medical facility. For example, the system enclosure may be formed from medical grade stainless steel or another medical grade material.

The system can also be used for cleansing and/or degreasing equipment such as food service equipment which may include, but are not limited to, ovens, ranges, fryers, grills, steam cookers, oven stacks, refrigerators, coolers, holding cabinets, cold food tables, worktables, ice machines, faucets, beverage dispensing equipment, beer dispensers, shelving, food displays, dish washing equipment, and grease traps. The system can also be used for water treatment (e.g., water purification, disinfection, and/or softening applications).

An ORP value can be used for water system monitoring to reflect the antimicrobial potential of a given sample of water. ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example, $E. coli$, $Salmonella$, $Listeria$, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground" voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone ($O_3$), an oxidizing agent approved for drinking water treatment by the U.S. Environmental Protection Agency. For instance, ozone is one of the strongest disinfectants approved for potable water treatment capable of inactivating bacteria, viruses, $Giardia$, and $Cryptosporidium$.

The disclosed system may be configured to output an AOS including water with an ORP of about 600 mV to about 1000 mV, with particular embodiments configured to output water having an ORP of about 850 mV at a flow rate of approximately 1.5 gallons per minute (GPM) to provide pathogenic control. Additionally, the system may be configured to reduce the surface tension of the water being used to cleanse and/or degrease hard surfaces and equipment by creating an AOS (e.g., a water and ozone solution) wherein the surface tension of the water is reduced from about 72 Millinewtons per meter at 20 degrees Centigrade to about 48-58 Millinewtons per meter at 20 degrees Centigrade to greatly improve the cleansing and/or degreasing qualities thereof.

FIGS. 1 through 7 illustrate a system 100 for generating aqueous ozone solution (AOS) with structural isolation between electronic components and fluid path(s) of the system 100, in accordance with one or more embodiments of this disclosure. The system 100 is configured to generate and mix ozone into water in order to output an AOS (e.g., a water and ozone solution). Although the system 100 is discussed with regard to applications that employ water to generate an AOS, it is contemplated that the system 100 may be also configured to generate other types of ozonated fluid solutions for the purposes of cleansing, degreasing, decontaminating, and/or fluid treatment.

Figure 2:
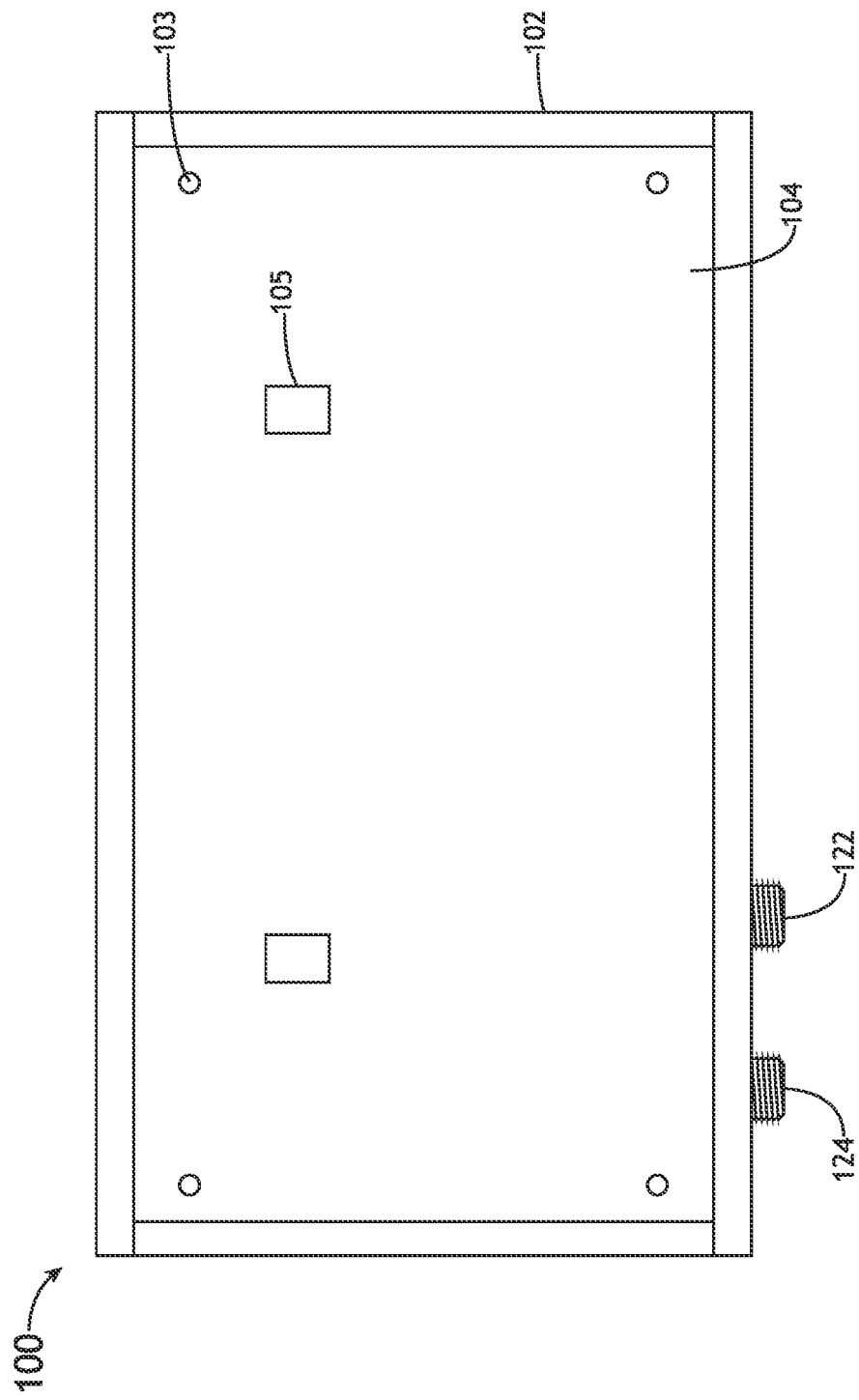
FIG. 2 is a rear view of the system for generating AOS, in accordance with one or more embodiments of this disclosure.
Figure 4:
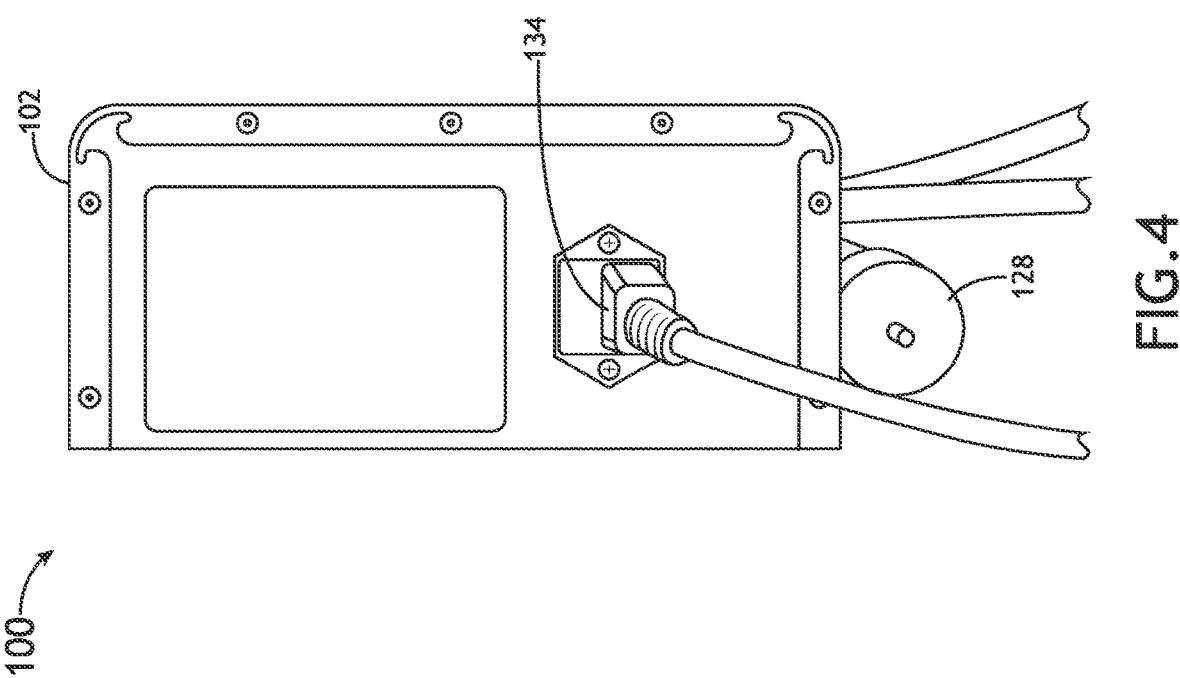
FIG. 4 is a right side view of the system for generating AOS, in accordance with one or more embodiments of this disclosure.

As shown in FIG. 1, the system 100 includes a system enclosure 102 with openings for a water inlet 122 and an AOS outlet 124. As shown in FIG. 2, the system enclosure 102 may have a removable backplate 104 that is configured to be secured to the system enclosure 102 by one or more fasteners 103 (e.g., screws to mate with bores in the system enclosure 102, latches, interference fit fasteners, clipping fasteners, magnetic fasteners, or the like). The system enclosure 102 may further include coupling portions to couple with a power source 134 (e.g., a power cable as shown in FIG. 4), a power button 136, an indicator light 138, an externally mounted air dryer 128, any combination thereof, and so forth.

Figure 3:
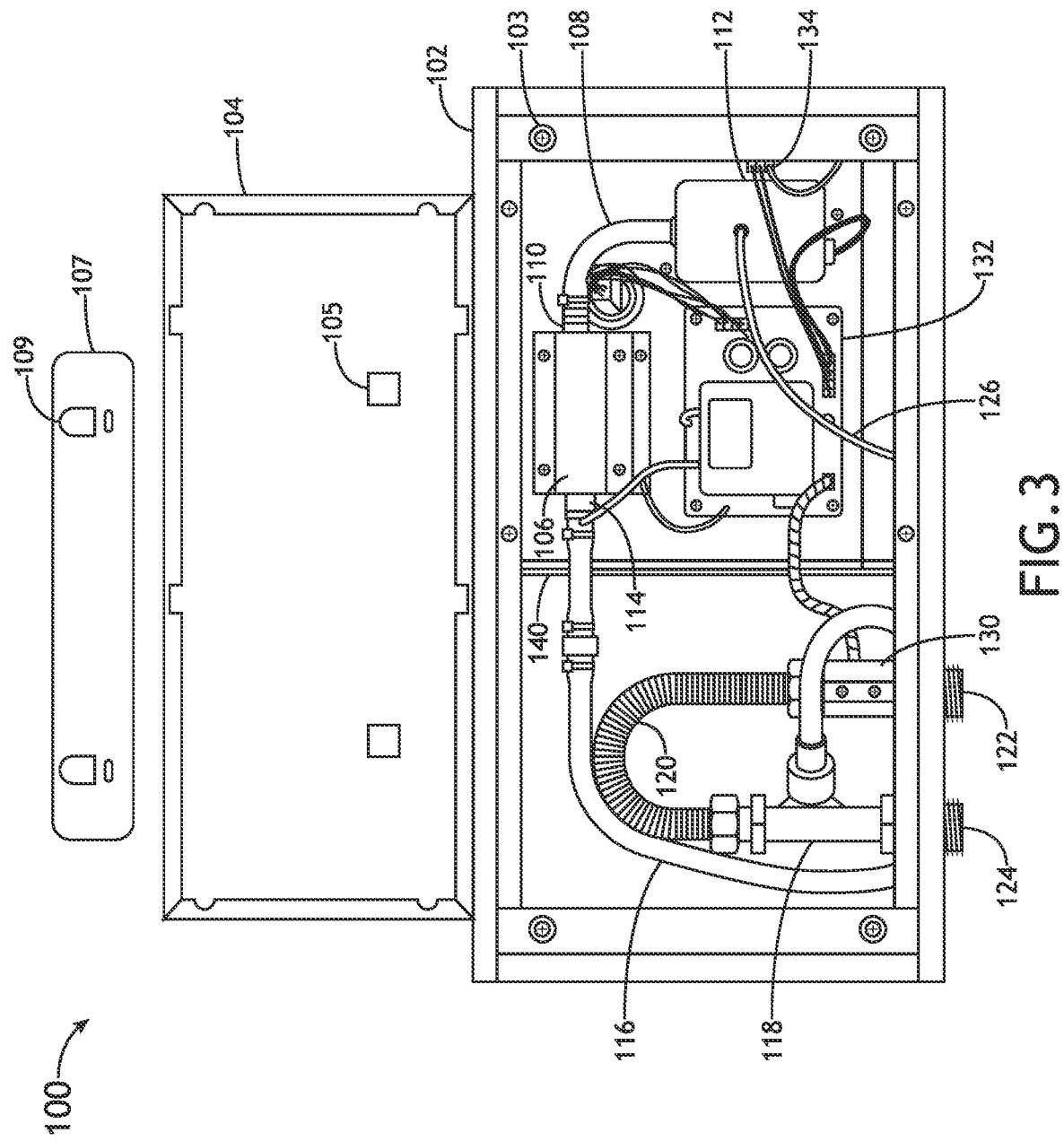
FIG. 3 is a rear view of the system for generating AOS, with a backplate removed to show internal components of the system, in accordance with one or more embodiments of this disclosure.

Referring now to FIGS. 2 and 3, the backplate 104 may be removably coupled to a mounting bracket 107 that is configured to be secured to a wall structure (e.g., any wall within a residential/commercial building or vehicle, or any other type of supportive frame, such as a metal frame, or a wheeled frame to make the system 100 transportable). As shown in FIG. 3, the mounting bracket 107 may include a plurality of mounting members 109 for coupling the mounting bracket 107 to the backplate 104 of the system 100. The mounting bracket 107 may further include a plurality of holes configured to receive fasteners (e.g., screws/bolts) to secure the mounting bracket 107 to the wall structure. As shown in FIGS. 2 and 3, the backplate 104 may include a plurality of slits/notches 105 that are configured to slide onto the mounting members 109 of the mounting bracket 107 so that the system 100 can be removably coupled to the wall structure by the mounting bracket 107. Any other type of removable coupling interface may be used to connect the system 100 to the mounting bracket 107 so that the system 100 can be easily attached or removed from the mounting bracket 107 without having to use any tools. This enables the system 100 to be interchanged, serviced, or reconfigured without having to unscrew or disassemble any fixed components to take down the system 100.

FIG. 3 is an illustration of the system 100 with the backplate 104 removed from the system enclosure 102, in accordance with one or more embodiments of this disclosure. As shown in FIG. 3, the system 100 includes one or more ozone generators 106 configured to be disposed within the system enclosure 102. The one or more ozone generators 106 include one or more air intake ports 110 configured to receive air (e.g., ambient air) via one or more tubes 108 (e.g., flexible tubing, pipes, etc.). In some embodiments, the system 100 further includes an air stabilizer 112 that is configured to hold air before the air is supplied to the one or more ozone generators 106 to generate ozone. For example, the air stabilizer 112 may be fluidically coupled to the one or more air intake ports 110 of the one or more ozone generators 106 via the one or more one or more tubes 108. The air stabilizer 112 may comprise a box or other shaped container (e.g., plastic, metal, or glass box/container) that defines a cavity within the system enclosure 102. This cavity defined by the air stabilizer 112 is configured to hold a volume of air in order to improve airflow to the one or more ozone generators 106 by preventing obstruction of the one or more tubes 108 and/or the one or more air intake ports 110. In some embodiments, the air stabilizer 112 is replaced or augmented by an air pump that assists with transferring air to the one or more ozone generators 106.

The one or more ozone generators 106 also include one or more ozone output ports 114 configured to output ozone generated by the one or more ozone generators 106. The one or more ozone output ports 114 may be coupled to a fluid mixer 118 via one or more tubes 116 (e.g., flexible tubing, pipes, etc.). The fluid mixer 118 is configured to mix the ozone into water flowing through the system 100 to generate AOS, as will be described in further detail below.

In embodiments, the one or more ozone generators 106 may include one or more corona discharge tubes configured to use oxygen in the air supplied via the one or more air intake ports 110 to generate ozone, such as through splitting of oxygen molecules in the air through electrical discharge caused by supplying power to a dielectric material within the corona discharge tube. The one or more ozone generators 106 are configured to convert oxygen from incoming air into ozone. The one or more ozone generators 106 may be powered by a power source 134 (e.g., power cord/adapter, which may comprise a 120V/240V power supply unit, power distribution circuit, or the like). In some embodiments, a power signal from power source may be transformed via a transformer suitable for applying the voltage to the dielectric within the corona discharge tube of an ozone generator.

The system 100 may include a relay 132 (e.g., a switchboard with analog or digital logic circuits) that controls distribution of power and/or communication signals within the system 100. For example, the relay 132 may be connected to the power source 134, a power button 136, an indicator light 138, the one or more ozone generators 106, and any sensors/switches (e.g., flow switch 130 and/or ORP monitor) of the system 100.

In some embodiments, the one or more ozone generators 106 may be operated at 110 volts/60 Hz and have an operating frequency of about 450 kHz and 550 kHz, with a power rating of less than about 15 watts, and with a unit performance for electrical consumption of about 32 watts. For example, the one or more ozone generators 106 may have an operating frequency of about 480 kHz. Further, the one or more ozone generators 106 can be provided according to ISO 9001 CE standards.

Each of the one or more ozone generators 106 may be configured to produce from about 800 mg ozone per hour to about 1200 mg ozone per hour, although other ranges may be appropriate depending on the application. In some embodiments, each of the one or more ozone generators 106 produces about 1000 mg ozone per hour. The one or more ozone generators 106 may include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

The system 100 may further include one or more air dryers 128 (or filters), which may be externally coupled to the system enclosure 102. The one or more air dryers 128 are configured to remove moisture from air before the air is supplied to the one or more ozone generators 106 through the one or more air intake ports 110. The one or more air dryers 128 may be configured to dry the air to a minus dew point by removing water vapor or moisture therefrom, where the water could inhibit the production of ozone by the one or more ozone generators 106. In some embodiments, the one or more air dryers 128 are configured to remove moisture from air before the air flows into the air stabilizer/pump 112. The one or more air dryers 128 may be fluidically coupled to the air stabilizer/pump 112 by one or more tubes 126 (e.g., flexible tubing, pipes, etc.) that extend through an opening in the system enclosure 102.

Figure 5:
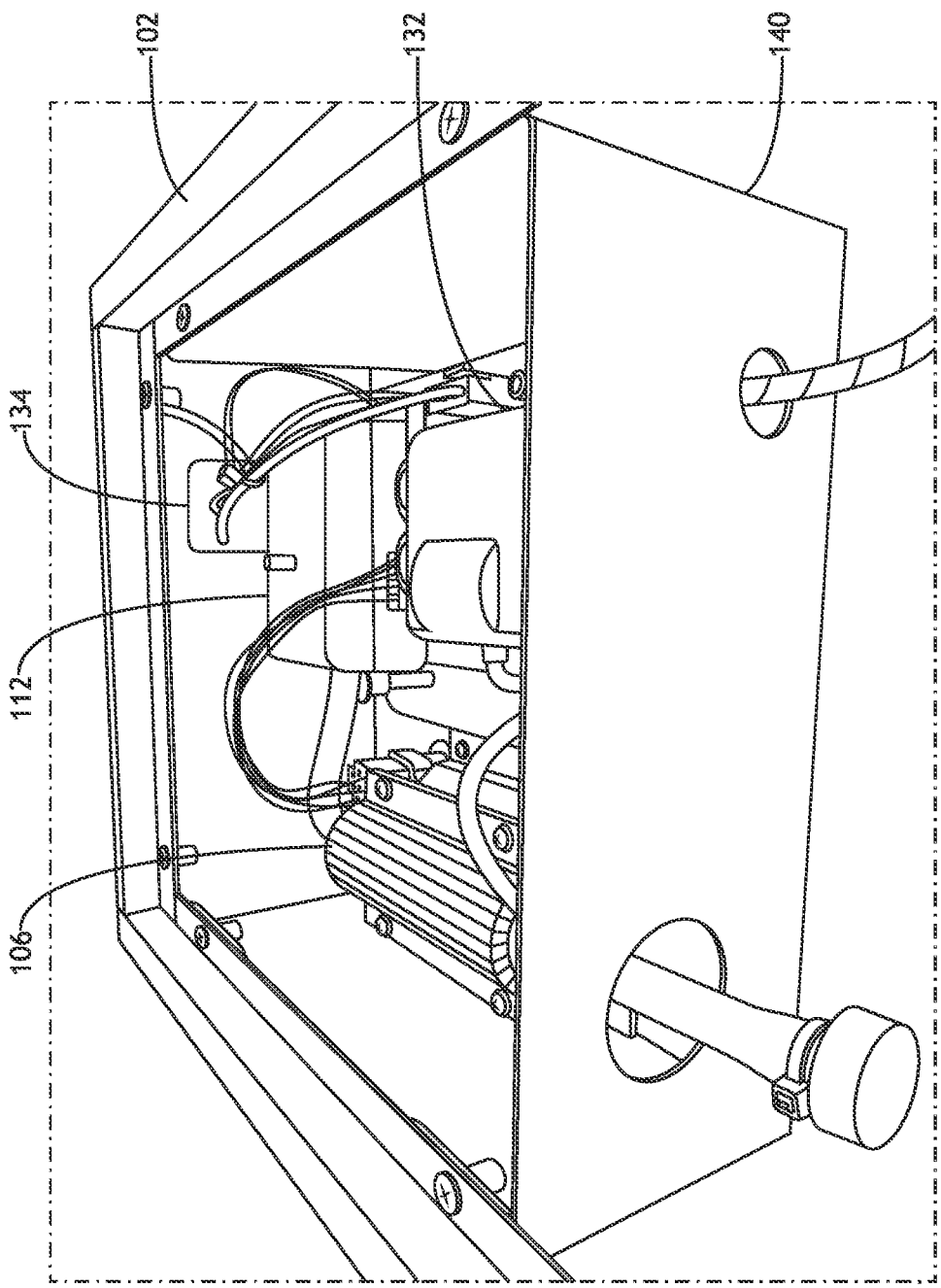
FIG. 5 is a perspective view of an internal portion of the system for generating AOS, including an internal cradle for mounting and isolating electronic components within the system, in accordance with one or more embodiments of this disclosure.

To reduce the risk of damage to electronic components from water/AOS leaks that may occur within the system enclosure 102, the system 100 includes a cradle 140 that provides structural isolation between electronic components and fluid path(s) within the system enclosure 102. As shown in FIG. 5, the cradle 140 is mounted within the system enclosure 102 via a plurality of fasteners that couple the cradle 140 to an inner rim of the system enclosure 102 so that the cradle 140 is fixed within the system enclosure 102. In some embodiments, the cradle 140 has a baseplate surrounded by a plurality of walls that extend from the base plate to the inner rim of the system enclosure 102. For example, the cradle 140 may have an open box-like structure. The cradle 140 has at least one wall that defines separate compartments within the system enclosure, including a first compartment for electronic components and a second compartment for a fluid path extending from the water inlet 122 to an AOS outlet 124. The first compartment may be defined by the cradle 140 itself while the second compartment is defined by remaining space within the system enclosure 102 that is outside the cradle 140. As noted above, these first and second compartments are separated by at least one cradle wall.

The first compartment contains the one or more ozone generators 106 and the relay 132, which are mounted to the cradle 140 (e.g., mounted to the baseplate on the inside of the cradle 140). The first compartment may further contain power source 134 connections, power button 136 and indicator light 138 connections, and the air stabilizer/pump 112. The cradle 140 structurally isolates the foregoing electronic components from the fluid path(s) between the water inlet 122 to an AOS outlet 124. Another advantage is that the cradle 140 also allows electronic components to be easily removed and replaced within the system enclosure 102 by unmounting and remounting the cradle 140. In some embodiments, the system 100 can be quickly serviced to replace defective electronics by swapping one cradle 140 (having the defective electronic components mounted thereon) with another cradle 140 (having the replacement electronic components mounted thereon).

Figure 6:
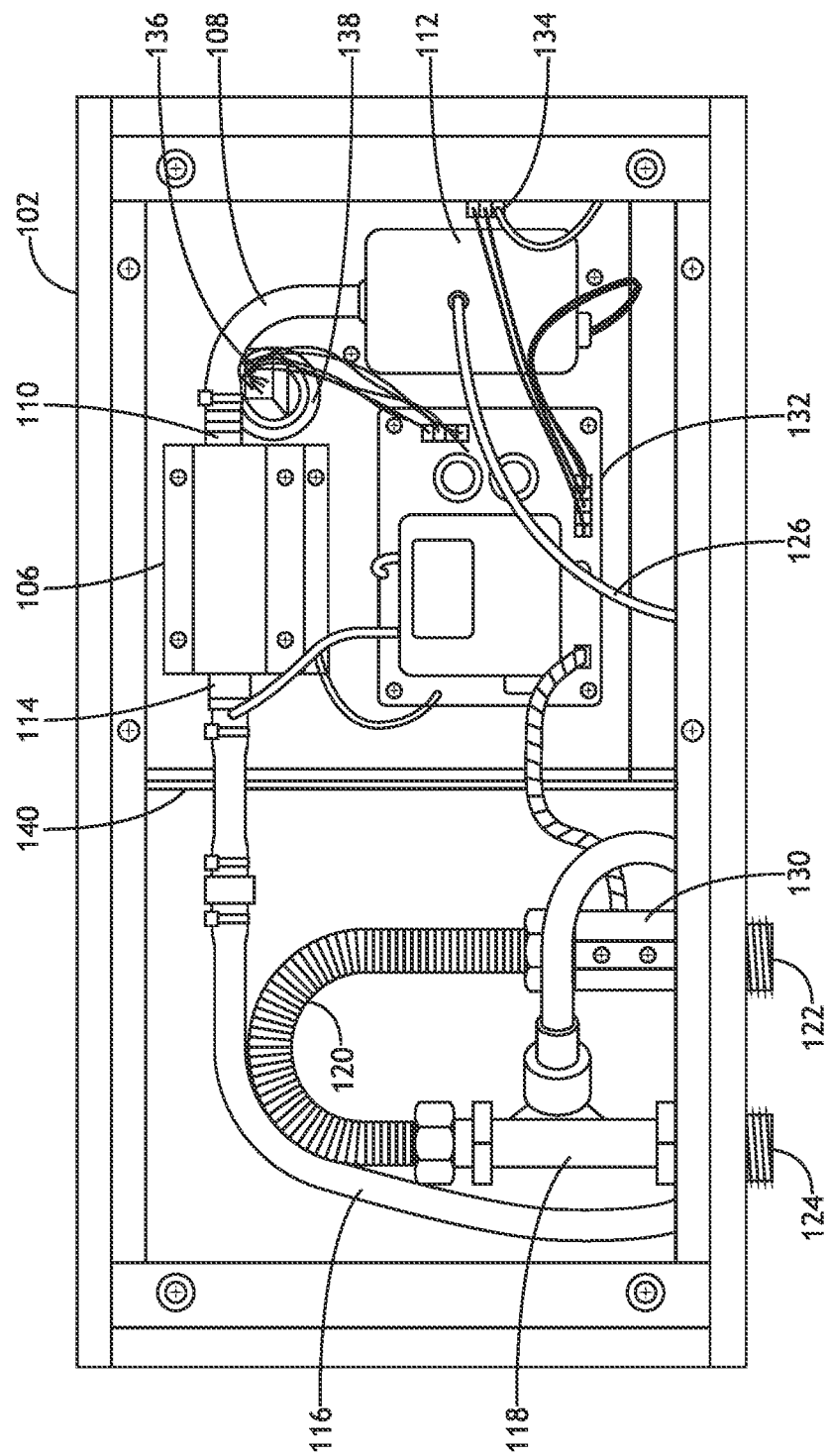
FIG. 6 is another rear view of the system for generating AOS, with the backplate removed to show internal components of the system, in accordance with one or more embodiments of this disclosure.

As shown in FIG. 6, the fluid mixer 118 is coupled to the one or more ozone generators 106 by one or more tubes 116 (e.g., flexible tubing, pipes, etc.) for transferring ozone from the one or more ozone generators 106 to the fluid mixer 118. In embodiments, the one or more tubes 116 extend across (e.g., over or through) the cradle 140 wall that separates the first and second compartments.

In preferred embodiments, the fluid mixer 118 is disposed within the system enclosure 102, fluidically coupled between the water inlet 122 and the AOS outlet 124. The fluid path between the water inlet 122 and the AOS outlet 124 is confined within the second compartment (i.e., outside of the cradle 140 wherein all/most of the electronic components are mounted). To accomplish this configuration, the water inlet 122 and the AOS outlet 124 may be connected by a U-shaped coupling 120 (e.g., a hose, tube, or pipe having a U-shaped bend) so that the water inlet 122 and the AOS outlet 124 positioned within the same compartment and at the same side of the system enclosure 102. Alternatively, the water inlet 122 and AOS outlet 124 may be connected by a straight line coupling if the water inlet 122 and AOS outlet 124 are within the same compartment but at opposite sides of the system enclosure 102, or the water inlet 122 and AOS outlet 124 may be connected by an L-shaped coupling if the water inlet 122 and AOS outlet 124 are within the same compartment but located at sides of the system enclosure 102 that are perpendicular to one another.

Figure 7:
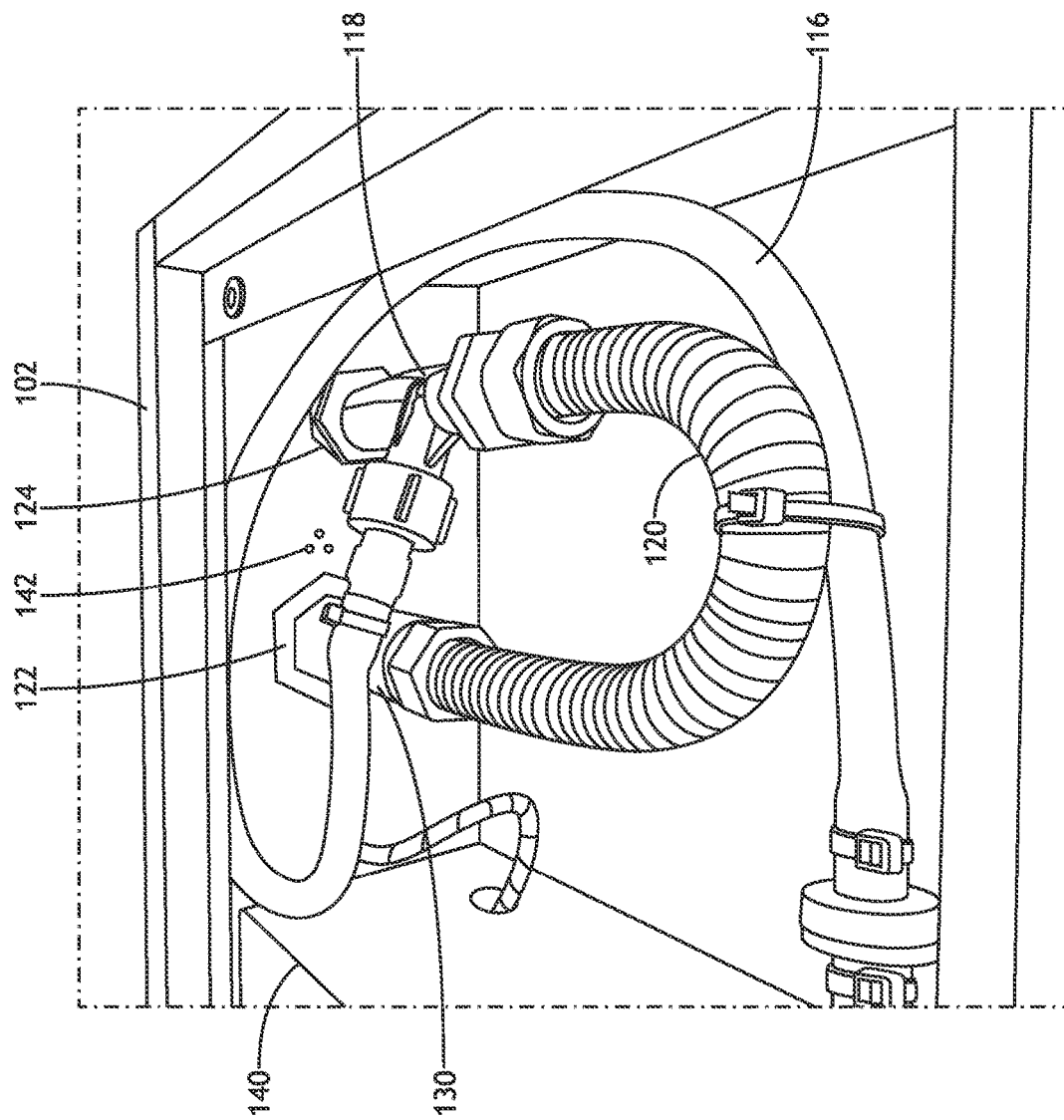
FIG. 7 is a perspective view of another internal portion of the system for generating AOS, including fluid paths that are isolated from the electronic components of the system by the internal cradle for mounting and isolating the electronic components within the system, in accordance with one or more embodiments of this disclosure.

As shown in FIG. 7, the system enclosure 102 may include one or more holes 142 adjacent to the water inlet 122 and/or water outlet 124. The one or more holes 142 are configured to allow any leaked water to drain out of the second compartment. If any water is leaked from the fluid path between the water inlet 122 and the AOS outlet 124, the water can be drained out of the second compartment through the one or more holes 142 without risk of spilling into the first compartment/cradle 140 and damaging any of the system electronics (e.g., ozone generator(s) 106, relay 132, etc.) that are mounted therein.

Referring again to FIG. 6, the fluid mixer 118 may be configured to introduce/inject ozone generated by the one or more ozone generators 106 into water flowing between the water inlet 122 and the AOS outlet 124. In this manner, the fluid mixer 118 mixes the ozone from the one or more ozone generators 106 with the water flowing into the system 100 to produce an AOS that is output via the AOS outlet 124.

The fluid mixer 118 may be a multi-port coupler including an inlet, an outlet, and an ozone input port between the inlet and the outlet. The multi-port coupler may simply be pipe/tube fittings with an ozone input port formed therein, 3-way pipe/tube fittings, or the like. In some embodiments, the multi-port coupler includes a venturi. A venturi can include an injector venturi design (e.g., a "T" design), where the venturi is coupled between the inlet and the outlet, and where ozone is introduced to the venturi through another port (i.e., the ozone input port) positioned perpendicular to the flow path of the water (from the inlet to the outlet). During operation, ozone generated by the one or more ozone generators 106 is drawn into the venturi and mixed with the water stream flowing from the inlet to the outlet. A pressure differential between the inlet and the outlet may serve to facilitate drawing the ozone into the venturi and to facilitate mixing of the ozone and the water. In some embodiments, a pressure differential greater than 20 psi inlet over outlet (e.g., at least a 20 psi difference between the inlet and the outlet, with pressure higher at the water inlet) is provided to generate negative suction in the venturi to thereby draw in the generated ozone, while assuring the energy for water flow and pressure for operation of the venturi.

In order to further increase effectiveness of the mixing process delivered by the venturi, the AOS may pass through an in-line mixer coupled between fluid mixer 118 (e.g., a venturi) and the AOS outlet 124. The in-line mixer can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the AOS. For example, water can have a surface tension of about 72 Millinewtons, whereas the solution of water and substantially uniform-sized ozone bubbles can have a surface tension of about 48-58 Millinewtons. In embodiments, the in-line mixer has an internal diameter that equals an internal diameter of the output port of a venturi to which the in-line mixer is coupled. The same internal diameter can provide an uninterrupted transition of the fluid flowing from the venturi to the in-line mixer, such as to maintain a vortex action or mixing action of the water and the ozone bubbles. The in-line mixer also provides increased contact time between the water and ozone bubbles and can facilitate preparation of uniform ozone bubble size. In some embodiments, the in-line mixer has a length of about two inches downstream from the venturi, which can allow sufficient time for the velocity of the vortex action caused by the pressure differential of the venturi to crush the gaseous bubbles entrained in the solution into uniformed size bubbles. The in-line mixer can also reintroduce undissolved gas back into the solution resulting in increased efficiency as well as reduced off-gas at the point of application. The in-line mixer can include multiple chambers through which the AOS flows. The size of the chambers can be determined based on the water flow (e.g., throughput), gas mixing, and desired time exposure. In some embodiments, the system 100 produces a stream of AOS at the AOS outlet 124 having a molar concentration of ozone of at least 20%, or more particularly at least 25%, far surpassing previous systems that have mass gas transfer rates of less than 10%.

The system 100 may further include or may be coupled with a flow switch 130 that is configured to detect water flow through the system 100. In some embodiments, the flow switch 130 may be disposed within the system enclosure 102. For example, the flow switch 130 may be fluidically coupled in-line with the fluid mixer 118, between the water inlet 122 and the AOS outlet 124. In other embodiments, the flow switch 130 may be external to the system enclosure 102 and/or at a distance from the system enclosure 102. For example, the flow switch 130 may be coupled to any of the fluid paths for water/AOS flow through the system 100.

The flow switch 130 can be configured to provide electric signals indicative of water/AOS flow through the system 100. For example, the flow switch 130 may be a mechanical flow switch/sensor, electromagnetic flow switch/sensor, pressure-based flow switch/sensor, optical flow switch/sensor, or the like, configured to provide an electric signal indicative of a flow of fluid (e.g., water/AOS) through the system 100. In some embodiments, the flow switch 130 may include solenoid-based flow switches/sensors, such as to avoid significant restriction of flow through the system 100.

In embodiments, the flow switch 130 is configured to transmit one or more control signals to the relay 132 in response to sensing a flow of water/AOS through the system 100. In response to receiving the one or more control signals, the relay 132 may cause the one or more ozone generators 106 to generate ozone. For example, the relay 132 may pass an activation and/or power signal onto the one or more ozone generators 106.

The flow switch 130 may be communicatively coupled to the relay 132 by one or more connectors (e.g., wires, cables, optical fibers, etc.) for transmitting signals between the flow switch 130 and the relay 132. In some embodiments, the one or more connectors extend across (e.g., over or through) the cradle 140 wall that separates the first and second compartments. In other embodiments, the system 100 may include a wireless communication interface (e.g., wireless receivers, transmitters, and/or transceivers) for receiving signals from the flow switch 130. For example, the flow switch 130 and the relay 132 may include wireless communication interfaces for sending/receiving wireless communication/control signals.

The system 100 may be configured to dispense an AOS (e.g., a water and ozone solution) having an ORP of between 600 mV and 1000 mV to provide pathogenic control without introduction of harsh treatment chemicals, such as chlorine. After operation of the system 100, the output AOS can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubbles can influence gas transfer characteristics. In some embodiments, the fluid mixer 118 and in-line mixer generate an ozone bubble size of about 2 to about 3 microns. For instance, micro-bubbles can be produced and/or sheared into uniformed micro-size bubbles as the solution passes through the fluid pathways.

Corona discharge ozone can be used virtually anywhere. Since ozone is made on site, as needed, and where needed, there is no need to ship, store, handle or dispose of it, nor any containers associated with shipping, storing, handling, and disposing of a treatment chemical, as is the situation with most chemicals utilized in water treatment.

The system 100 may be configured to provide indications pertaining to the operation status of the system 100, such as to ensure proper operation, or to provide an indication regarding a need for adjustment, servicing, or maintenance. For example, the flow switch 130 may be configured to send the signal to an indicator light 138 located on an exterior of the system enclosure 102 to provide a visual indication that the system 100 is turned on and/or an indication that fluid (e.g., water/AOS) is flowing through the system 100. In some embodiments, the indicator light 138 is always on when the system 100 is turned on (i.e., after pressing the power button 136 to turn the system 100 on). In other embodiments, the indicator light 138 may be configured to illuminate (or change color) upon receiving a signal from the flow switch 130 to indicate active water flow through the system 100. The indicator light 138 may also be coupled to a sensor (e.g., a relay) configured to measure that a voltage is applied to ozone generators 106. When a proper voltage is applied to the one or more ozone generators 106, the sensor can send a signal to the indicator light 138. In some embodiments, the indicator light 138 will provide a visual indication when each sensor and the flow switch 130 provide their respective signals to the relay 132. For example, the relay 132 can be coupled to the power source 134, power button 136, and flow switch 130. The relay 132 may be configured to send an activation signal to the indicator light 136 when the power source 134 is providing power to the one or more ozone generators 106 (i.e., after the power button 136 is pressed on). Optionally, the relay 132 may be further configured to send the activation signal to the indicator light 136 only when the flow switch 130 also provides one or more signals regarding fluid flow through the system 100, or the relay 132 may be configured to send a signal that causes the indicator light 136 to change color when the power and water flow conditions are both met. In such a configuration, the indicator light 138 can verify that the system 100 is operating under design conditions (e.g., having an active flow of water and having a sufficient power supply to the one or more ozone generators 106).

In some embodiments, the power button 136 is mounted to a frontside of the system enclosure 102, and the indicator light 138 comprises one or more LEDs or another type of light source that form ring-shaped illumination around the power button 136. For example, the indicator light 138 may comprise a ring-shaped LED array that surrounds the power button 136 or any type of backlight that forms a ring by providing illumination behind the power button 136.

The system 100 may include an in-line ORP monitor (e.g., ORP sensor/meter) positioned to measure the ORP of AOS dispensed from the AOS outlet 124, coupled within a distribution line, or the like. The in-line ORP monitor can be coupled with the relay 132, such that the in-line ORP monitor provides a signal to the relay 132 upon detection of a desired ORP or range of ORPs (e.g., at least 600 mV, at least 650 mV, at least 700 mV, at least 750 mV, at least 800 mV, at least 850 mV, at least 900 mV, at least 950 mV, etc.). The relay 132 can then provide an activation (or color change) signal to the indicator light 138 upon proper functioning of the system 100 (e.g., when the power source is providing power to the one or more ozone generators 106, when the flow switch 130 provides one or more signals regarding fluid flow through the system 100, and when the in-line ORP monitor detects a desired ORP of the AOS generated by the system 100). When the indicator light 138 is not activated (or the wrong color), this can provide an indication that a component or components of the system 100 may need adjustment, servicing, or maintenance. Alternatively, the system 100 can be configured to activate the indicator light 138 upon failure of one or more of the components of the system 100 (e.g., no power supplied to the one or more ozone generators 106, no flow of water detected by the flow switch 130, or an out of range ORP detected by the in-line ORP monitor).

By providing an ORP of between 600 mV and 1000 mV with the system 100, the output AOS can be utilized to destroy various pathogens, including, but not limited to, algae (e.g., blue-green), bacteria (e.g., *Aeromonas* & *Actinomycetes*, *Bacillus*, *Campylobacters*, *Clostridium botulinum*, *Escherichia coli* (*E. coli*), *Flavobacterium*, *Helicobacter* (*pylori*), *Heterotrophic* Bacteria, *Legionella pneumophila*, *Micrococcus*, *Mycobacterium tuberculosis*, *Pseudomonas aeruginosa*, *Salmonella*, *Shigella shigellosis* (dysentery), *Staphylococcus* sp, *albus*, *aureus*, *Streptococcus*, *Vibrio: alginolyticus*, *anguillarium*, *parahemolyticus*, *Yersinia enterocolitica*), fungi, molds, yeasts, mold spores, nematodes, protozoa (e.g., *Acanthamoeba* & *Naegleria*, *Amoeboe Trophozoites*, *Cryptosporidium*, *Cyclospora*, *Entamobea* (*histolytica*), *Giardia lamblia*, *Giardia muris*, *Microsporidium*, *N. gruberi*), *trematodes*, viruses (e.g., Adenovirus, Astrovirus, Cailcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

In some implementations, incoming water may have a surface tension of about 72 Millinewtons per meter at 20° C. as it enters the system 100. The system 100 may be configured to reduce the surface tension of the water in the resulting AOS to about 48-58 Millinewtons per meter at 20° C. The reduced surface tension of the water enables the AOS being sprayed onto the hard surfaces and equipment to remove grease more effectively from hard surfaces and equipment since ozonated fluid is more capable of loosening and disintegrating any biofilm on the hard surfaces or equipment. The reduced surface tension of the water in the AOS better enables the cleansing of the hard surfaces and equipment since it more easily penetrates foreign material on the hard surfaces and equipment.

The AOS can be used for a variety of applications including, but not limited to: cleansing and/or degreasing hard surfaces such as plastic, glass, ceramic, porcelain, granite, stainless steel, aluminum, or the like; cleansing and/or degreasing equipment such as food service equipment such as ovens, ranges, fryers, grills, steam cookers, oven stacks, refrigerators, coolers, holding cabinets, cold food tables, worktables, ice machines, faucets, beverage dispensing equipment, beer dispensers, shelving food displays, dish washing equipment, grease traps, or the like; and/or cleansing and/or degreasing HVAC or plumbing systems such as roof top units, air scrubbers, humidifiers, water heaters, pumps, or the like.

In embodiments, the system 100 further includes a water input line configured to supply water from a water source (e.g., a conventional water main/supply line, or the like) to the system 100. For example, the water input line may have a connector for connecting to a conventional water source (e.g., to a faucet) on one end and may be fluidically coupled to the water inlet 122 of the system 100 on the other end. In some embodiments, the water input line may further include a shutoff valve to turn on/off water supplied to the system 100 and/or control the rate at which water is supplied to the system 100. In some embodiments, the water input line includes or is coupled to a sediment filter configured to remove particulates (e.g., sand, silt, dirt, rust, etc.) from water before the water enters the system 100.

The system 100 is configured to produce an AOS (as described above) by mixing ozone into the water. The AOS is then output from the system 100 via the AOS outlet 124 which may be coupled to an AOS output line. In some embodiments, AOS output line may also include a shutoff valve for selectively enabling or disabling the flow of AOS through the AOS output line. In some embodiments, the AOS output line includes or is coupled to the ORP monitor. Additionally, the ORP monitor may be communicatively coupled with an ORP monitor control unit. The ORP monitor control unit may be configured to display the ORP value sensed by the ORP monitor, calibrate the ORP monitor, program ORP setpoints for the system 100, and/or communicate the ORP value or control signals based on the ORP value to the relay 132 of the system 100.

Although the invention has been described with reference to embodiments illustrated in the attached drawings, equivalents or substitutions may be employed without departing from the scope of the invention as recited in the claims. Components illustrated and described herein are examples of devices and components that may be used to implement embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A system for generating aqueous ozone solution, comprising:
   a system enclosure, the system enclosure including one or more openings for a water inlet and an aqueous ozone solution outlet;
   a cradle mounted within the system enclosure, the cradle including a wall that defines separate compartments within the system enclosure, including a first compartment for electronic components and a second compartment for a fluid path extending from the water inlet to the aqueous ozone solution outlet, wherein the first compartment is defined by the cradle itself while the second compartment is defined by remaining space within the system enclosure that is outside the cradle;
   an ozone generator mounted to the cradle, within the first compartment;
   a relay mounted to the cradle, within the first compartment, the relay being configured to selectively activate the ozone generator; and
   a fluid mixer disposed within the second compartment, the fluid mixer being fluidically coupled to the ozone generator via one or more tubes extending across the wall, the fluid mixer being configured to inject ozone generated by the ozone generator into water received from a water source via the water inlet to produce an aqueous ozone solution that is output via the aqueous ozone solution outlet.

2. The system of claim 1, wherein the fluid mixer comprises a venturi.

3. The system of claim 1, further comprising:
   a flow switch fluidically coupled in between the water inlet and the aqueous ozone solution outlet, the flow switch configured to generate a signal indicative of water flow between the water inlet and the aqueous ozone solution outlet.

4. The system of claim 3, wherein the relay is configured to selectively activate the ozone generator in response to the signal generated by the flow switch.

5. The system of claim 4, wherein the flow switch is communicatively coupled to the relay by one or more wires extending across the wall.

6. The system of claim 1, further comprising:
an air dryer externally mounted to the system enclosure, wherein the air dryer is fluidically coupled to the ozone generator.

7. The system of claim 6, further comprising:
an air stabilizer or pump fluidically coupled between the air dryer and the ozone generator, the air stabilizer or pump being mounted to the cradle, within the first compartment.

8. The system of claim 1, wherein the system enclosure includes one or more holes adjacent to the water inlet and the water outlet, the one or more holes being configured to drain any leaked water out of the second compartment.

9. The system of claim 1, wherein the water inlet and water outlet are connected by a U-shaped coupling.

10. The system of claim 1, further comprising:
a mounting bracket for attaching the system to a wall structure; and
a backplate for the system enclosure, wherein the backplate includes slits or notches configured to slide onto mounting members of the mounting bracket in order to removably couple the backplate to the wall structure.

11. A system for generating aqueous ozone solution, comprising:
a system enclosure, the system enclosure including one or more openings for a water inlet and an aqueous ozone solution outlet;
a power button mounted to a frontside of the system enclosure;
a ring-shaped indicator light surrounding the power button;
a cradle mounted within the system enclosure, the cradle including a wall that defines separate compartments within the system enclosure, including a first compartment for electronic components and a second compartment for a fluid path extending from the water inlet to the aqueous ozone solution outlet, wherein the first compartment is defined by the cradle itself while the second compartment is defined by remaining space within the system enclosure that is outside the cradle;
an ozone generator mounted to the cradle, within the first compartment;
a relay mounted to the cradle, within the first compartment, the relay being configured to selectively activate the ozone generator and the ring-shaped indicator after the power button is pressed to turn on the system; and
a fluid mixer disposed within the second compartment, the fluid mixer being fluidically coupled to the ozone generator via one or more tubes extending across the wall, the fluid mixer being configured to inject ozone generated by the ozone generator into water received from a water source via the water inlet to produce an aqueous ozone solution that is output via the aqueous ozone solution outlet.

12. The system of claim 11, wherein the fluid mixer comprises a venturi.

13. The system of claim 11, further comprising:
a flow switch fluidically coupled in between the water inlet and the aqueous ozone solution outlet, the flow switch configured to generate a signal indicative of water flow between the water inlet and the aqueous ozone solution outlet.

14. The system of claim 13, wherein the relay is configured to selectively activate the ozone generator in response to the signal generated by the flow switch after the power button is pressed to turn on the system.

15. The system of claim 14, wherein the flow switch is communicatively coupled to the relay by one or more wires extending across the wall.

16. The system of claim 11, further comprising:
an air dryer externally mounted to the system enclosure, wherein the air dryer is fluidically coupled to the ozone generator.

17. The system of claim 16, further comprising:
an air stabilizer or pump fluidically coupled between the air dryer and the ozone generator, the air stabilizer or pump being mounted to the cradle, within the first compartment.

18. The system of claim 11, wherein the system enclosure includes one or more holes adjacent to the water inlet and the water outlet, the one or more holes being configured for any leaked water to drain out of the second compartment.

19. The system of claim 11, wherein the water inlet and the water outlet are connected by a U-shaped coupling.

20. The system of claim 11, further comprising:
a mounting bracket for attaching the system to a wall structure; and
a backplate for the system enclosure, wherein the backplate includes slits or notches configured to slide onto mounting members of the mounting bracket in order to removably couple the backplate to the wall structure.

\* \* \* \* \*